US00PP26241P2

(12) United States Plant Patent
de Groot

(10) Patent No.: US PP26,241 P2
(45) Date of Patent: Dec. 15, 2015

(54) ***HYPERICUM* PLANT NAMED 'RUIHYH006B'**

(50) Latin Name: *Hypericum×inodorum*
Varietal Denomination: Ruihyh006b

(71) Applicant: Henk C. A. de Groot, Amstelveen (NL)

(72) Inventor: Henk C. A. de Groot, Amstelveen (NL)

( * ) Notice: Subject to any disclaimer, the term of this patent is extended or adjusted under 35 U.S.C. 154(b) by 121 days.

(21) Appl. No.: 13/998,760

(22) Filed: Dec. 3, 2013

(51) Int. Cl.
*A01H 5/02* (2006.01)

(52) U.S. Cl.
USPC ..... Plt./442

(58) Field of Classification Search
USPC ..... Plt./442, 263.1, 226
CPC ..... A01H 5/02; A01H 5/00
See application file for complete search history.

(56) References Cited

PUBLICATIONS

PLUTO UPOVROM Plant Variety Database as per CA PBR 12-7756, Oct. 31, 2012, 1 page.*

* cited by examiner

*Primary Examiner* — Kent L Bell
(74) *Attorney, Agent, or Firm* — Penny J. Aguirre

(57) ABSTRACT

A new cultivar of *Hypericum×inodorum*, 'Ruihyh006b', that is characterized by its compact plant habit suitable for container growing, its medium sized berries that are light orange-pink in color and rounded in shape, and its small sized, light green sepals.

2 Drawing Sheets

Botanical classification: *Hypericum×inodorum.*
Variety denomination: 'Ruihyh006b'.

BACKGROUND OF THE INVENTION

The present invention relates to a new and distinct cultivar of *Hypericum×inodorum* and will be referred to hereafter by its cultivar name, 'Ruihyh006b'. 'Ruihyh006b' is a semi-evergreen shrub grown for use as a landscape plant and container plantings.

The new cultivar was derived from a controlled breeding program conducted by the Inventor in Hazerswoude, The Netherlands. The overall purpose of the breeding program was to develop new cultivars of *Hypericum* plants with different shapes and sizes of berries and with resistance to *Melampsora hypericorum.*

The new cultivar arose from a cross made by the Inventor in Hazerswoude, The Netherlands in April 2007 between 'White Hypearl' (not patented) as the female parent and 'Jolly Hypearl' (not patented) as the male parent. The Inventor selected 'Ruihyh006b' as a single unique plant amongst the seedlings that resulted from the above cross in autumn of 2008.

Asexual propagation of the new cultivar was first accomplished by the Inventor by vegetative stem cuttings in 2010 in Hazerswoude, The Netherlands. Asexual propagation by vegetative stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Ruihyh006b' as a unique cultivar of *Hypericum.*

1. 'Ruihyh006b' exhibits a compact plant habit suitable for container growing.
2. 'Ruihyh006b' exhibits medium sized berries that are light orange-pink in color and round in shape.
3. 'Ruihyh006b' exhibits small sized, light green sepals.

The female parent of 'Ruihyh006b', 'White Hypearl', differs from 'Ruihyh006b' in having berries that are white in color. The male parent of 'Ruihyh006b', 'Jolly Hypearl', differs from 'Ruihyh006b' in having berries that are red in color, narrower in width, and longer in length. 'Ruihyh006b' can be most closely compared to the cultivar 'Hot Hypearl' (not patented). 'Hot Hypearl' is similar to 'Ruihyh006b' in having berries that are rounded in shape. 'Hot Hypearl' differs from 'Ruihyh006b' in having berries that are red in color.

BRIEF DESCRIPTION OF THE DRAWINGS

The accompanying colored photographs illustrate the overall appearance and distinct characteristics of the new *Hypericum*. The plants in the photographs were taken of plants two years in age as grown in a one-gallon container in a greenhouse in Lelystad, The Netherlands.

The photograph in FIG. 1 provides a side view of 'Ruihyh006b' in bloom.

Figure 1:
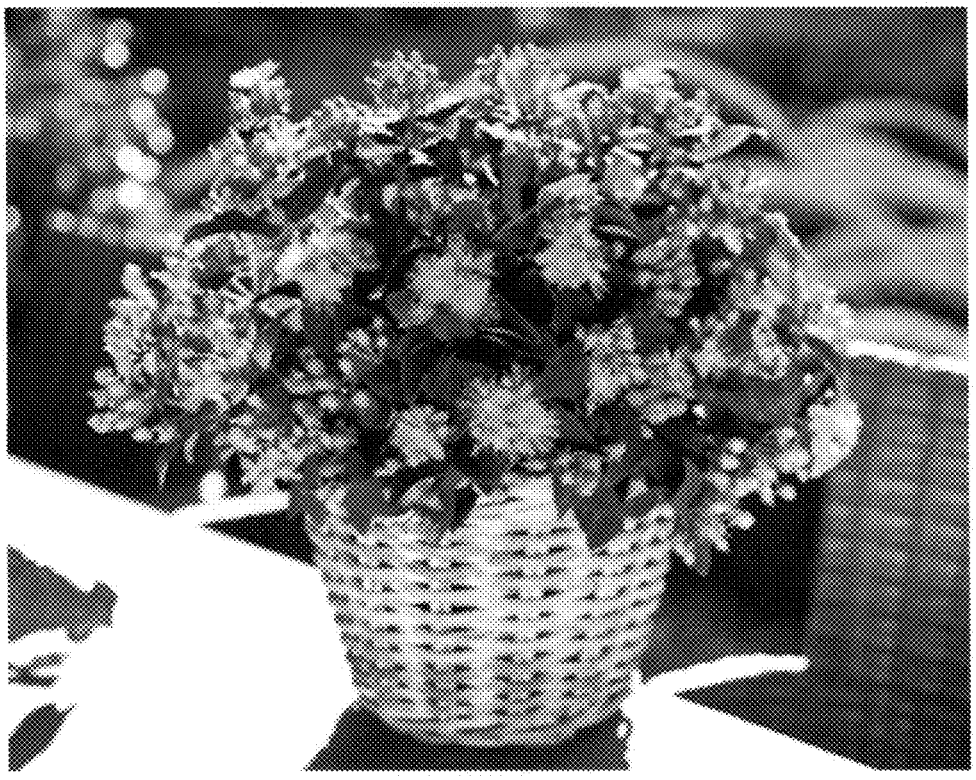
Figure 2:
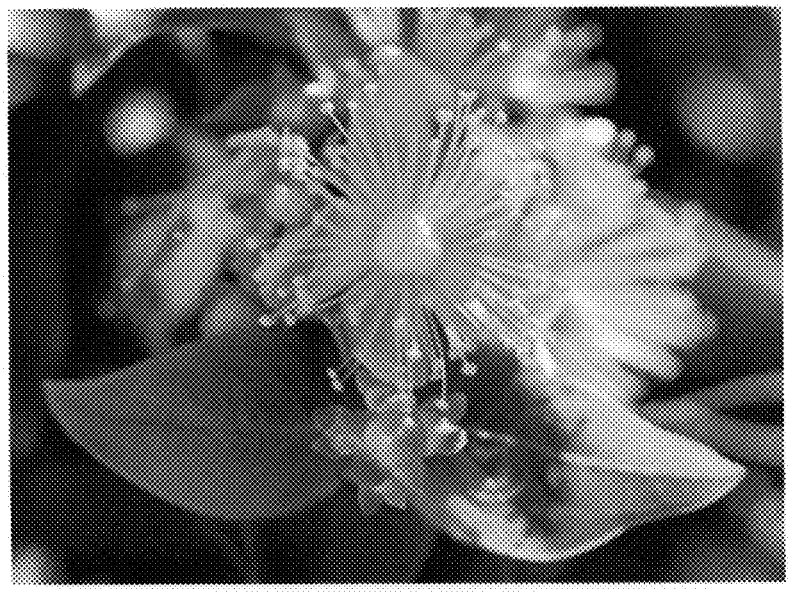

The photograph in FIG. 2 provides a close-up view of a flower of 'Ruihyh006b'.

Figure 3:
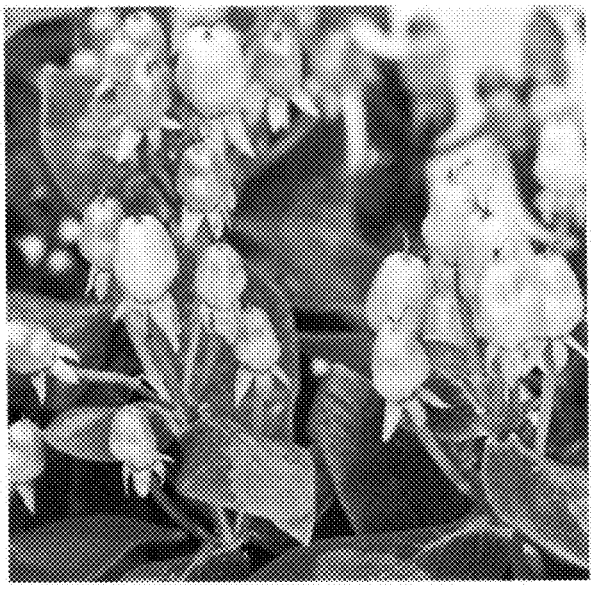

The photograph in FIG. 3 provides a close-up view of the berries of 'Ruihyh006b'.

The colors in the photographs are as close as possible with the digital photography techniques available, the color values cited in the detailed botanical description accurately describe the colors of the new *Hypericum.*

DETAILED BOTANICAL DESCRIPTION

The following is a detailed description of two year-old plants of the new cultivar as grown outdoors in 2-gallon containers in Davidsonville, Md. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—From July to September in The Netherlands.

*Plant type*.—Semi-evergreen shrub.

*Plant habit*.—Compact with suitability for container growing.

*Height and spread*.—Reaches an average of 35 cm in height and spread.

*Cold hardiness*.—Observed to be hardy to at least −10° C.

*Diseases*.—Has shown tolerance to *Melampsora hypericorum*.

*Root description*.—Fibrous and fine.

*Propagation*.—Vegetative stem cuttings.

*Growth rate*.—Moderate, typical for cultivars of *Hypericum×inodorum*.

Stem description:

*Shape*.—Round.

*Stem color*.—New growth; 144A to 144B, maturing branches become a blend of 166A to 166B and 175A as they become woody.

*Stem size*.—Main stems; an average of 1.5 cm in diameter and 20 cm in length, lateral branches; an average of 15 cm in length and 4 mm in width.

*Stem surface*.—Glabrous when young and maturing, exfoliating when mature.

*Internode length*.—Average of 2 cm.

*Branching*.—Freely branched with lateral branches held at an average angle of 30° to vertical.

Foliage description:

*Leaf shape*.—Ovate to lanceolate.

*Leaf division*.—Simple.

*Leaf base*.—Cuneate.

*Leaf apex*.—Acute to rounded.

*Leaf fragrance*.—None.

*Leaf venation*.—Pinnate, not conspicuous, a blend of 137C and 138B in color on upper and lower surface.

*Leaf margins*.—Entire.

*Leaf arrangement*.—Opposite, slightly cupped downward, aspect is horizontal to slightly upward.

*Leaf attachment*.—Sessile.

*Leaf substance*.—Moderate.

*Leaf surface*.—Glabrous on upper and lower surface.

*Leaf size*.—Up to 5.4 cm in length, up to 3.5 cm in width.

*Leaf color*.—Newly expanded leaves; upper surface 143A and lower surface, 144B, mature leaves; upper surface N189A, lower surface a blend of 137C and 138B in color.

Inflorescence description:

*Inflorescence type*.—Terminal compound corymb.

*Flower buds*.—Conical in shape with acute to rounded apex, an average of 8 mm in length and 3.5 mm in width prior to opening, calyx portion is wrapped around petals and 144B in color, petal portion emerges N144A in color and changes to 154A to 154C prior to opening.

*Flower fragrance*.—None detected.

*Flower quantity*.—About 12 per lateral branch.

*Flower type*.—Complete, rotate with deeply reflexed petals and prominent stamens and ovary.

*Flower aspect*.—Upward facing.

*Flower lastingness*.—About 5 days.

*Flower size*.—Average of 2.3 cm in diameter and 1.8 cm depth.

*Petals*.—5, oblong to round in shape, un-fused, curved inward and becoming horizontal, upper surface is glabrous and lower surface is satiny, entire margin, truncate base, rounded apex with single slight notch, about 1.2 cm in length and 7 mm in width, color is 14A (opening and mature, lower and upper surface).

*Calyx*.—Reflexed, un-fused sepals, about 1.1 cm in diameter and 3 mm in depth.

*Sepals*.—5, oblong in shape, upper and lower surface; 143C in color and glabrous in texture, up to 5 mm in length and 3 mm in width, entire margin, round-truncate base, acute apex.

*Peduncles*.—An average of 9 mm in length and 1.5 mm in width, 144A to 144B in color, glabrous surface.

*Pedicels*.—An average of 1.5 cm in length and 1 mm in width, 144A to 144B in color, glabrous surface.

Reproductive organs:

*Gynoecium*.—Compound pistil about 6 mm in length and 4 mm in width, styles; 3, 1B to 1C in color, an average of 2 mm in length and 0.3 mm in width, stigmas; 3, 22A in color about 0.3 mm in diameter, ovary is superior and 1B to 1C in color, an average of 6 mm in length and 4 mm in width.

*Androecium*.—Numerous stamens (an average of 60), spreading outward from base of ovary extending about 1.8 cm in diameter, filaments are 7A in color, an average of 8 mm in length and 0.4 mm in width, anthers are 7A in color, dorsifixed, about 1 mm in length and width, pollen was not visible.

*Fruit*.—Fruit; conical in shape with mucronate apex, glabrous and satiny surface, an average of 9 mm in length and 6 mm in width, color a blend of 180B, 180C, 179B and 179C.

It is claimed:

1. A new and distinct cultivar of *Hypericum* plant named 'Ruihyh006b' as herein illustrated and described.

* * * * *